United States Patent
Larson et al.

(10) Patent No.: US 11,412,960 B2
(45) Date of Patent: Aug. 16, 2022

(54) PEDESTAL FOR SENSOR ASSEMBLY PACKAGING AND SENSOR INTRODUCER REMOVAL

(71) Applicant: MEDTRONIC MINIMED, INC., Northridge, CA (US)

(72) Inventors: Eric Allan Larson, Simi Valley, CA (US); Alejandro J. Urrutia-Gamez, Granada Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 883 days.

(21) Appl. No.: 15/688,603

(22) Filed: Aug. 28, 2017

(65) Prior Publication Data

US 2019/0059796 A1 Feb. 28, 2019

(51) Int. Cl.
| | | |
|---|---|---|
| *A61B 5/145* | (2006.01) | |
| *B65B 55/02* | (2006.01) | |
| *A61B 5/1486* | (2006.01) | |
| *B65B 5/04* | (2006.01) | |
| *A61M 5/00* | (2006.01) | |
| *A61B 5/00* | (2006.01) | |
| *B65B 7/28* | (2006.01) | |
| *A61B 5/1473* | (2006.01) | |

(52) U.S. Cl.
CPC ........ *A61B 5/14532* (2013.01); *A61B 5/1486* (2013.01); *A61B 5/14865* (2013.01); *A61B 5/6849* (2013.01); *A61M 5/003* (2013.01); *B65B 5/04* (2013.01); *B65B 55/02* (2013.01); *A61B 5/0031* (2013.01); *A61B 5/1473* (2013.01); *A61B 5/14503* (2013.01); *A61B 5/6848* (2013.01); *A61B 2560/0456* (2013.01); *A61B 2560/063* (2013.01); *B65B 7/2842* (2013.01)

(58) Field of Classification Search
CPC . A61B 5/14532; A61B 5/1473; A61B 5/1486; A61B 5/14865; A61B 5/6849; A61B 2560/063; A61B 5/14503; A61B 5/150022

See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |

(Continued)

*Primary Examiner* — Allen Porter
*Assistant Examiner* — Michael A Catina
(74) *Attorney, Agent, or Firm* — Fortem IP LLP; Mary Fox

(57) ABSTRACT

A pedestal for a physiological characteristic sensor assembly and a physiological characteristic sensor assembly is provided. The pedestal includes a first side opposite a second side. The pedestal includes a sidewall that interconnects the first side and the second side. The pedestal also includes a first end opposite a second end. The pedestal includes at least one post that extends from the first side adjacent to the first end to couple the pedestal to a physiological characteristic sensor of the physiological characteristic sensor assembly. The pedestal also includes a recess defined in the sidewall at the second end. The recess has a first portion in communication with a second portion. The first portion has a first length that is less than a second length of the second portion along a perimeter of the sidewall, and the second portion is positionable to apply a force to the physiological characteristic sensor.

16 Claims, 14 Drawing Sheets

(56) References Cited

U.S. PATENT DOCUMENTS

| | | |
|---|---|---|
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | Melvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,101,305 B2 | 8/2015 | Larson et al. |
| 9,295,786 B2 | 3/2016 | Gottlieb et al. |
| 2007/0123819 A1 | 5/2007 | Mernoe et al. |
| 2008/0269687 A1* | 10/2008 | Chong .................. A61L 27/28 604/180 |
| 2009/0299301 A1 | 12/2009 | Gottlieb et al. |
| 2010/0160861 A1 | 6/2010 | Causey, III et al. |
| 2012/0227358 A1* | 9/2012 | Larson .................. B65B 5/04 53/425 |
| 2012/0296187 A1* | 11/2012 | Henning ............ A61B 5/14503 600/347 |
| 2015/0297822 A1 | 10/2015 | Larson et al. |
| 2016/0008028 A9 | 1/2016 | Matsumoto et al. |
| 2016/0174884 A1 | 6/2016 | Gottlieb et al. |
| 2017/0231497 A1 | 8/2017 | Brister et al. |

* cited by examiner

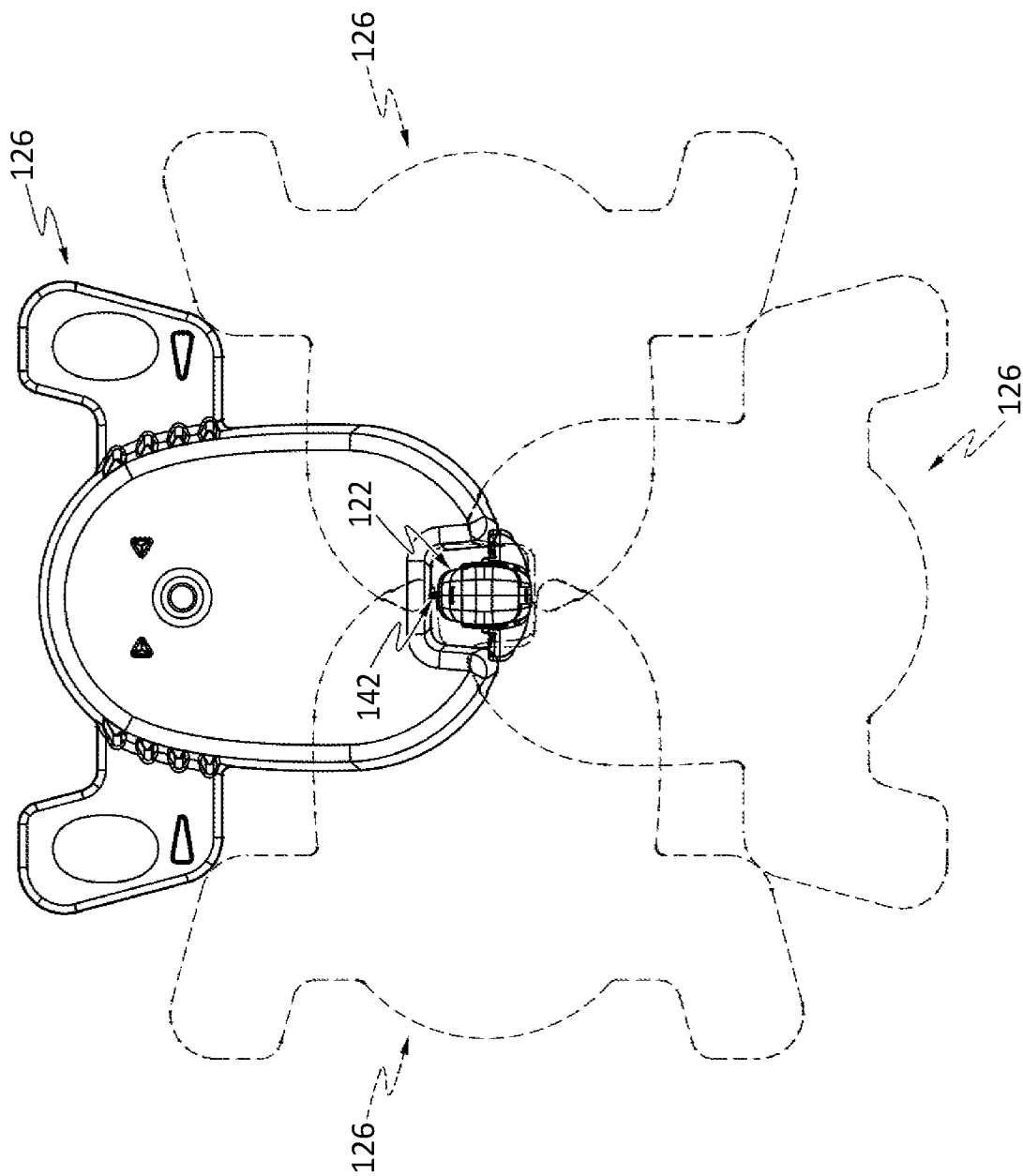

PEDESTAL FOR SENSOR ASSEMBLY PACKAGING AND SENSOR INTRODUCER REMOVAL

TECHNICAL FIELD

Embodiments of the subject matter described herein relate generally to medical devices, such as a physiological characteristic sensor assembly and a pedestal for use with a physiological characteristic sensor assembly. More particularly, embodiments of the subject matter relate to a pedestal, which is used for packaging a physiological characteristic sensor assembly during shipping and is also used to remove a sensor introducer once the physiological characteristic sensor is coupled to a user. In various embodiments, the physiological characteristic sensor is a glucose sensor.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

A glucose sensor of the type described above may be packaged and sold as a product that includes certain features or components that allow the user to position and subcutaneously implant the sensor. For example, thin film glucose sensors are often implanted subcutaneously/transcutaneously using a sensor introducer tool, which may be packaged with the glucose sensor. The sensor introducer contains a needle that is used to puncture the skin of a user at the same time as the sensor is introduced. The needle is then withdrawn, leaving the sensor in the skin of the user. The sensor introducer, commonly including the needle, is then discarded after inserting the sensor at the sensor site.

As the sensor introducer contains a needle, it is desirable to ship or otherwise package the sensor introducer so as to protect a user from contacting the needle during removal from the packaging. Further, in certain instances, it may be desirable to insert the glucose sensor at a sensor site that may be somewhat unconventional. For example, it may be desirable to insert the glucose sensor at a sensor site on an upper arm. In these instances, due to the position of the sensor introducer at the sensor site, it may be difficult to remove the sensor introducer while holding the glucose sensor at the sensor site.

Accordingly, it is desirable to provide a pedestal, which is coupled to the physiological characteristic sensor assembly, such as a glucose sensor assembly, for packaging purposes and for protecting the needle of the sensor introducer during shipping and removal from the packaging. Moreover, it is desirable to provide a pedestal, which is useable to remove the sensor introducer once the physiological characteristic sensor, such as a glucose sensor, is introduced at the sensor site. Furthermore, other desirable features and characteristics will become apparent from the subsequent detailed description and the appended claims, taken in conjunction with the accompanying drawings and the foregoing technical field and background.

BRIEF SUMMARY

According to various embodiments, provided is a pedestal for a physiological characteristic sensor assembly. The pedestal includes a first side opposite a second side. The pedestal includes a sidewall that interconnects the first side and the second side. The pedestal also includes a first end opposite a second end. The pedestal includes at least one post that extends from the first side adjacent to the first end to couple the pedestal to a physiological characteristic sensor of the physiological characteristic sensor assembly. The pedestal also includes a recess defined in the sidewall at the second end. The recess has a first portion in communication with a second portion. The first portion has a first length that is less than a second length of the second portion along a perimeter of the sidewall, and the second portion is positionable to apply a force to the physiological characteristic sensor.

Also provided according to various embodiments is a physiological characteristic sensor assembly. The physiological characteristic sensor assembly includes a physiological characteristic sensor. The physiological characteristic sensor includes a sensor coupled to a sensor base. The physiological characteristic sensor assembly includes an adhesive patch coupled to the physiological characteristic sensor. The physiological characteristic sensor assembly also includes a pedestal removably coupled to the physiological characteristic sensor. The pedestal includes a first side opposite a second side. The pedestal includes a sidewall that interconnects the first side and the second side. The pedestal also includes at least one post that extends from the first side and forms an interference fit with the sensor base. The pedestal also includes a recess defined through the sidewall having a first portion in communication with a second portion. The first portion has a first length that is less than a second length of the second portion along a perimeter of the sidewall, and the second portion is positionable over the sensor base to apply a force to the sensor base.

Further provided according to various embodiments is a physiological characteristic sensor assembly. The physiological characteristic sensor assembly includes a glucose sensor. The glucose sensor includes a sensor base having a first base side opposite a second base side. The physiological characteristic sensor assembly includes an adhesive patch coupled to the second base side of the sensor base. The adhesive patch defines at least one coupling bore. The physiological characteristic sensor assembly includes a pedestal having a first side removably coupled to the adhesive patch and the second base side and an opposite second side. The pedestal includes a sidewall that interconnects the first side and the second side. The pedestal has a first end opposite the second end. The pedestal also includes at least one post that extends outwardly from the first side adjacent to the first end and forms an interference fit with the sensor base. The at least one post is received through the at least one coupling bore of the adhesive patch. The pedestal also includes a recess defined through the sidewall at the second end. The recess has a first portion in communication with a second portion. The first portion has a first length that is less than a second length of the second portion along a perimeter of the sidewall, and the second portion is positionable over the first base side to apply a force to the sensor base.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 14 is a perspective view of the pedestal, which illustrates the various positions of the pedestal for applying a holding force to a portion of the physiological characteristic sensor to enable removal of the sensor introducer.

DETAILED DESCRIPTION

Figure 1:
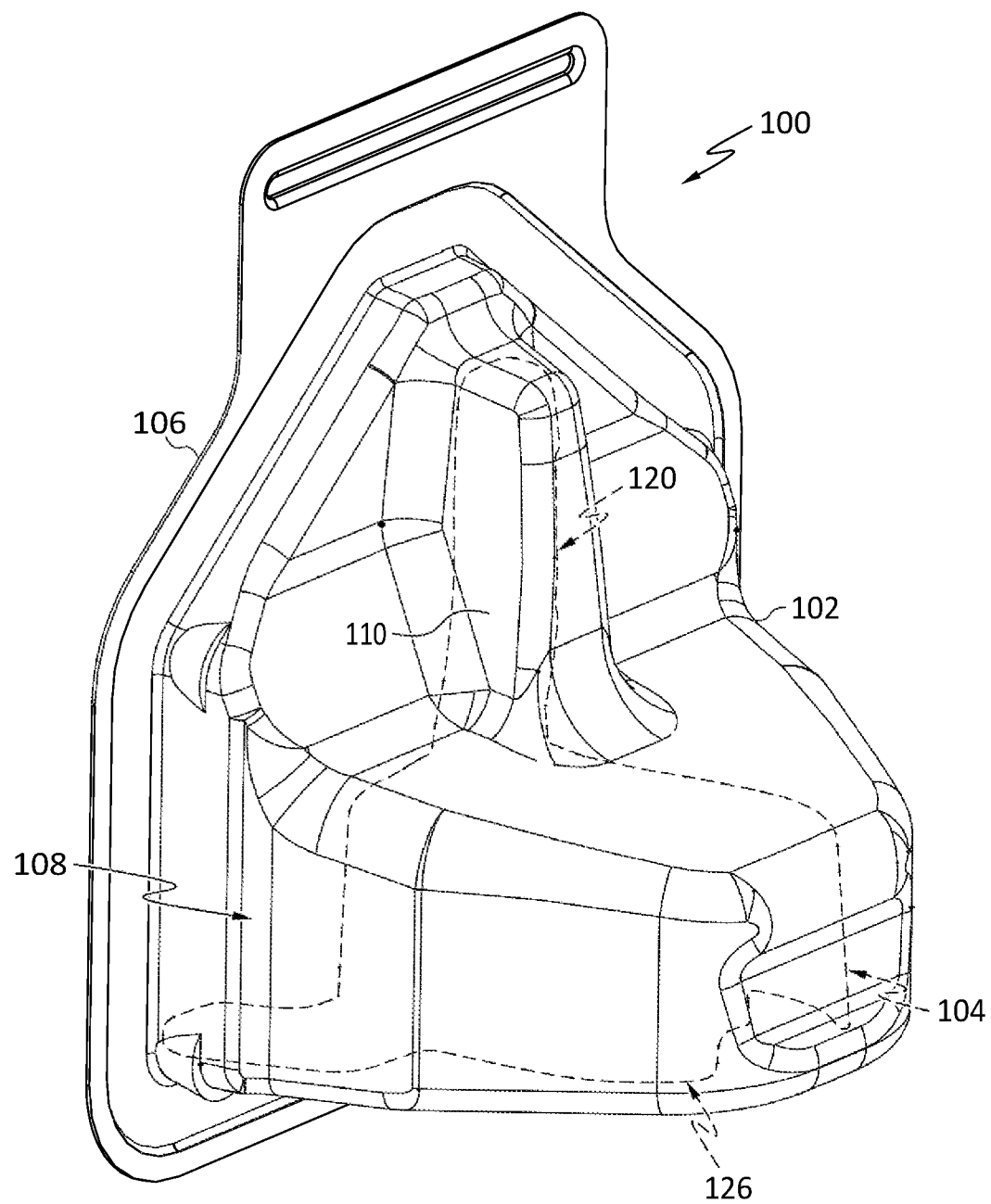
FIG. 1 is a rear perspective view of an exemplary embodiment of a physiological characteristic sensor assembly that includes a pedestal for sensor assembly packaging and sensor introducer removal enclosed in a package tray according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

The following description relates to various embodiments of a pedestal. The geometry of the pedestal enables the pedestal to be coupled to a physiological characteristic sensor, such as a glucose sensor, to provide a force that enables a user to remove a sensor introducer from the physiological characteristic sensor (and the sensor insertion site or sensor site). Stated another way, the pedestal, as described herein, enables a user to insert a glucose sensor at an unconventional location, such as an upper arm, lower back or other hard to reach location, and remove the sensor introducer with a single hand, while holding the physiological characteristic sensor at the sensor site with the pedestal. It should be noted that while the pedestal is described herein as being used with a glucose sensor, it will be understood that the pedestal may be employed with a variety of other sensors and/or medical devices. Thus, while the non-limiting examples described below relate to a medical device used to treat diabetes (more specifically, a pedestal for a glucose sensor), embodiments of the disclosed subject matter are not so limited.

Generally, the glucose sensor employed with the pedestal is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein).

Figure 2:
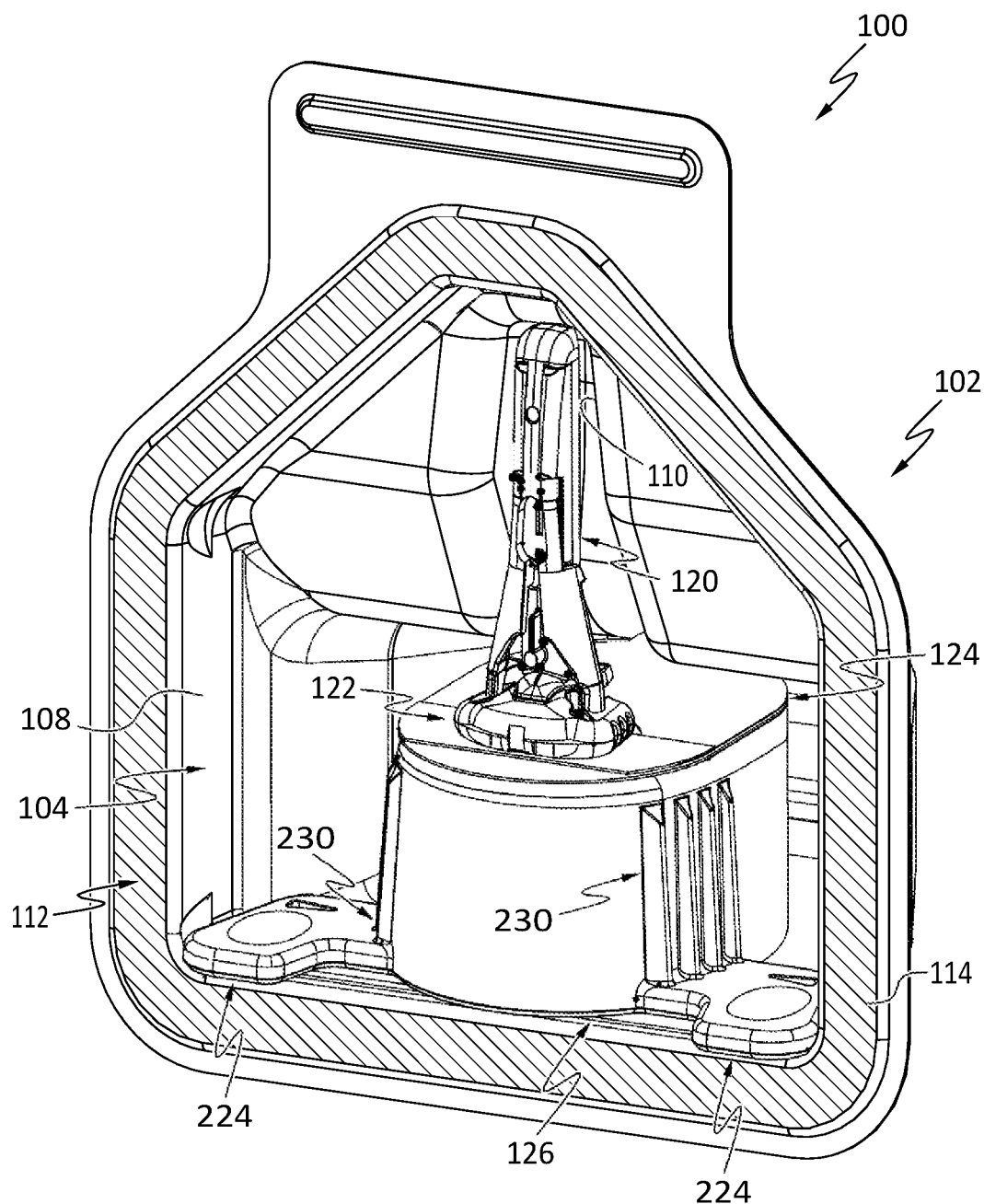
FIG. 2 is a front perspective view of the sensor assembly of FIG. 1, which includes the pedestal, in which a material is removed from a package tray to provide access to the physiological characteristic sensor assembly.

With reference to FIG. 1, FIG. 1 is a rear perspective view of an exemplary embodiment of a sensor package 100, and FIG. 2 is a front perspective view of the sensor package 100. The sensor package 100 represents one exemplary form factor that can be used for purposes of boxing, shipping, storing, and distributing physiological characteristic sensors, such as glucose sensors, which have been manufactured, assembled, and sterilized. In one example, the sensor package 100 generally includes, but is not limited to: a package tray 102; a physiological characteristic sensor assembly 104 (shown in phantom); and a piece of material 106.

In certain embodiments, the package tray 102 is composed at least in part from a plastic material. For the embodiment described here, the package tray 102 is formed as a one-piece molded plastic component. The package tray 102 is formed as a solid component that is free of holes, tears, punctures, etc. In practice, the package tray 102 may be formed from a thermoformed or injection molded plastic material such as, without limitation: polypropylene, polycarbonate (PC), acrylonitrile butadiene styrene (ABS), a PC/ABS blend, nylon, polyvinyl chloride (PVC), and polyethylene terephthalate glycol (PETG) material. In this example, the package tray 102 is composed of a polyethylene terephthalate glycol (PETG) material. The package tray 102 can be formed from a transparent or clear plastic material such that the physiological characteristic sensor assembly 104 is visible.

The physiological characteristic sensor assembly 104 is positioned within an interior cavity 108 of the package tray 102. Generally, the interior cavity 108 is shaped and sized in a manner that generally conforms to the physiological characteristic sensor assembly 104. In this regard, the package tray 102 may include a retaining feature 110 (also shown in FIG. 1) that accommodates a component of the physiological characteristic sensor assembly 104. The retaining feature 110 protects a portion of the physiological characteristic sensor assembly 104 during shipping and handling. Referring to FIG. 2, the front of the package tray 102 includes an opening 112 that leads to the interior cavity 108. The front of the package tray 102 also includes a sealing surface 114, which surrounds the opening 112. For ease of illustration, the sealing surface 114 is shaded in FIG. 2. Generally, the material 106 (FIG. 1) covers the opening 112 and is coupled to the package tray 102 in a manner that forms a seal between the sealing surface 114 and the material 106. In other words, the material 106 serves as a cover that encloses the physiological characteristic sensor assembly 104 within the interior cavity 108.

Figure 3:
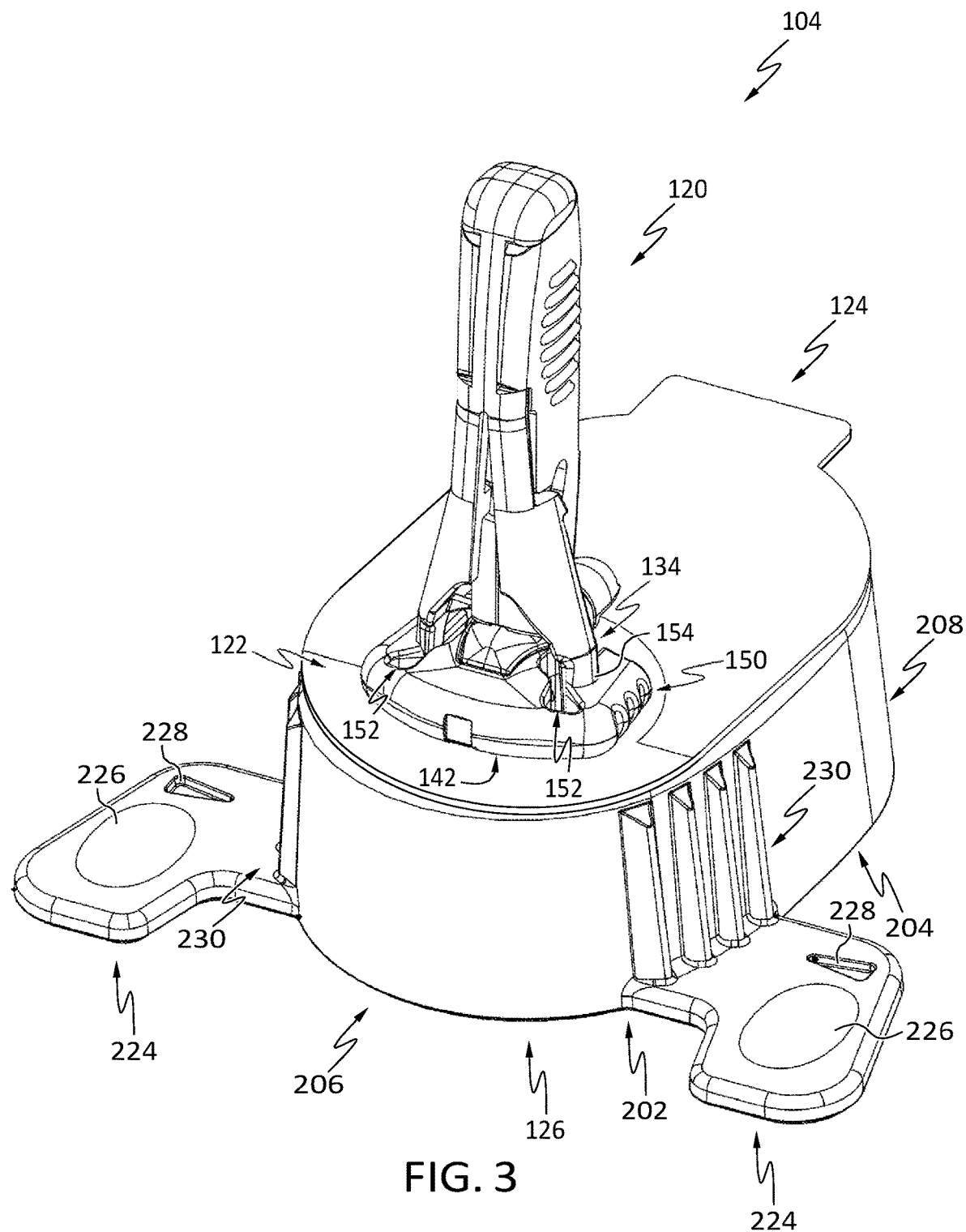
FIG. 3 is a perspective view of the physiological characteristic sensor assembly of FIG. 1, which includes the pedestal, and illustrates an inserter device exploded from the physiological characteristic sensor assembly.

With reference to FIG. 3, the physiological characteristic sensor assembly 104 is shown. In one example, the physiological characteristic sensor assembly 104 includes a sensor inserter or sensor introducer 120, a physiological characteristic sensor 122, an adhesive patch 124 and a pedestal 126. As depicted in FIG. 1 and FIG. 2, the components of the physiological characteristic sensor assembly 104 are coupled together as a single unit for placement in the package tray 102. Many features, aspects, and characteristics of the physiological characteristic sensor assembly 104 and its individual elements are conventional and, as such, will not be described in detail here. In addition, as will be discussed further herein, an insertion device 130 (FIG. 4) may be used by a user to remove the sensor introducer 120, the physiological characteristic sensor 122 and the adhesive patch 124 from the pedestal 126, and used to insert the physiological characteristic sensor 122 at a sensor insertion site or sensor site.

Figure 4:
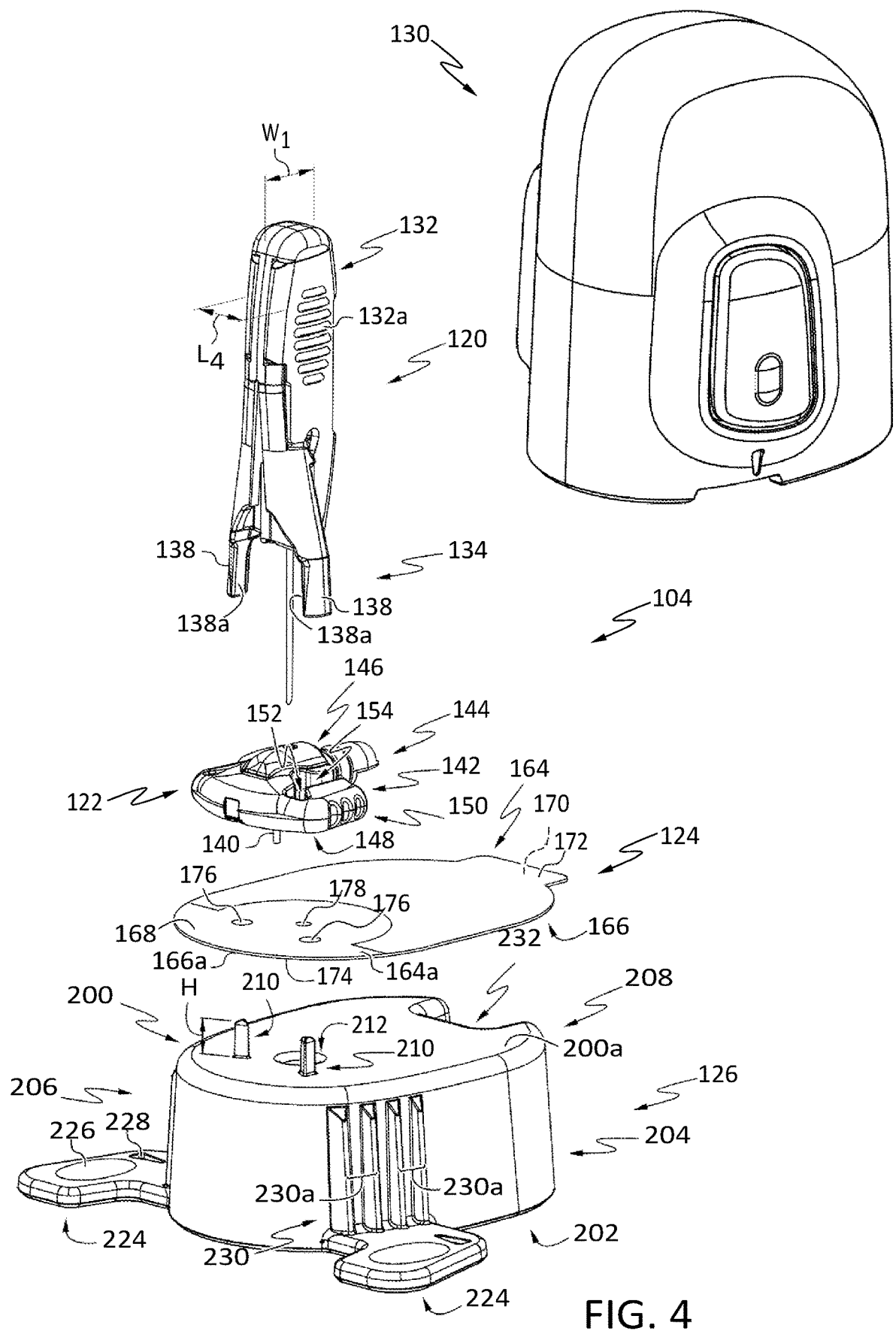
FIG. 4 is an exploded view of the physiological characteristic sensor assembly of FIG. 1, which includes the pedestal and the insertion device.

With reference to FIG. 4, an exploded view of the physiological characteristic sensor assembly 104 is shown, along with the insertion device 130. The sensor introducer 120 is manipulated to introduce a portion of the physiological characteristic sensor 122 into the body of the user. The sensor introducer 120 includes a body having a first end 132 and an opposite second end 134. The first end 132 defines a graspable portion 132a, which enables the user to manipulate the sensor introducer 120. The second end 134 includes a spring loaded insertion needle 136 and a pair of opposed mating projections 138. FIG. 4 depicts the insertion needle 136 in its extended position, where the insertion needle 136 protrudes from the body of the sensor introducer 120.

Each of the pair of mating projections 138 engage corresponding features on a portion of the physiological characteristic sensor 122 to couple the sensor introducer 120 to the physiological characteristic sensor 122 before introducing a portion of the physiological characteristic sensor 122 into the body of the user. The sensor introducer 120 and the physiological characteristic sensor 122 can be pre-connected as part of a sensor set, which could also include a sensor electronics module (not shown), such as a wireless transmitter that communicates with an infusion pump, a monitor device, or the like, which connects to the physiological characteristic sensor 122 after the insertion or deployment of a portion of the physiological characteristic sensor 122 in the body of the user. Alternatively, the sensor introducer 120 and the physiological characteristic sensor 122 can be packaged and provided together, as depicted in FIG. 2. In certain embodiments the sensor introducer 120 is composed at least in part from a plastic material. For the embodiment described here, the bulk of the sensor introducer 120 is formed as a molded plastic component. In practice, the sensor introducer 120 may be formed from ABS, nylon, an ABS/PC blend, PVC, polytetrafluoroethylene (PTFE), polypropylene, polyether ether ketone (PEEK), polycarbonate or the like. In one example, the sensor introducer 120 is formed from polycarbonate.

In one example, the physiological characteristic sensor 122 includes a glucose sensor 140 and a sensor base 142. It should be noted that the physiological characteristic sensor 122 is not limited to a glucose sensor, but rather, various other physiological characteristic sensors may be employed. The glucose sensor 140 may be provided as an integral part of the sensor base 142, as depicted in FIG. 4. The sensor base 142 gives structural support to the glucose sensor 140, and facilitates entry of the glucose sensor 140 into the body of the user. The glucose sensor 140 is an electrochemical sensor that includes the glucose oxidase enzyme, as is well understood by those familiar with glucose sensor technology. The glucose oxidase enzyme enables the glucose sensor 140 to monitor blood glucose levels in a diabetic patient or user by effecting a reaction of glucose and oxygen. Again, although certain embodiments pertain to glucose sensors, the manufacturing and packaging technology described here can be adapted for use with any one of the wide variety of sensors known in the art. Generally, the glucose sensor 140 is positionable in subcutaneous tissue of the user by the insertion needle 136 of the sensor introducer 120 to measure the glucose oxidase enzyme.

The sensor base 142 is coupled to the sensor introducer 120 and is coupled to the pedestal 126. The sensor base 142 includes a body 144 that defines a first base side 146 opposite a second base side 148. The body 144 is coupled to the sensor introducer 120 prior to the deployment of the glucose sensor 140 into the subcutaneous tissue of the user such that the first base side 146 is adjacent to the second end 134 of the sensor introducer 120. The second base side 146 is coupled to the adhesive patch 124. The sensor base 142 may also feature electrical and physical interfaces and elements that accommodate the sensor electronics module (not shown), such as the wireless transmitter that communicates with the infusion pump, the monitor device, or the like. In certain embodiments the sensor base 142 is composed at least in part from a plastic material. For the embodiment described here, the bulk of the sensor base 142 is formed as a molded plastic component. In one example, the sensor base 142 is formed from ABS, nylon, an ABS/PC blend, PVC, polytetrafluoroethylene (PTFE), polypropylene, polyether ether ketone (PEEK), polycarbonate, or the like. In this example, the sensor base 142 is composed of polycarbonate.

Figure 5A:
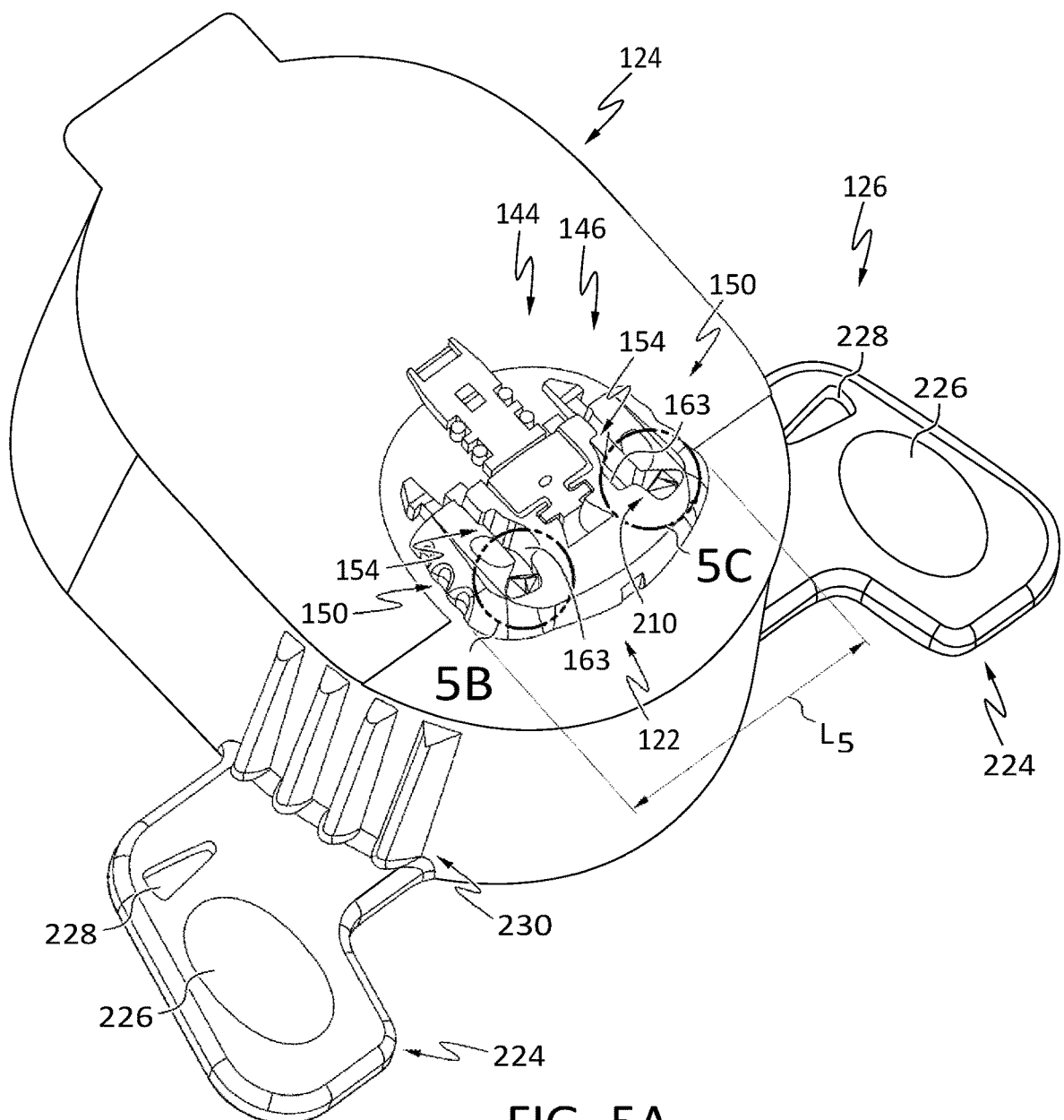
FIG. 5A is a top perspective view of a physiological characteristic sensor and an adhesive patch coupled to the pedestal of the physiological characteristic sensor assembly of FIG. 1.

With reference to FIG. 5A, the body 144 is shown in greater detail. The body 144 also includes a pair of wings 150, a pair of pedestal coupling pockets 152 and a pair of introducer coupling slots 154. Each of the pair of wings 150 are coupled to a first end 144a of the body 144 so as to movable or flexible relative to the body 144. In one example, the pair of pedestal coupling pockets 152 provide for a reduced thickness of the body 144 at an end of each of the wings 150, which enables the wings 150 to move or flex. The wings 150 couple the sensor base 142 to the electronics module (not shown), such as the wireless transmitter, which can communicate the sensor signals from the glucose sensor 140 to the infusion pump, the monitor device, or the like.

The pair of pedestal coupling pockets 152 is defined on opposite sides of the body 144 at the first end 144a of the body 144 so as to extend through the body 144 from the first base side 146 to the second base side 148. The pair of pedestal coupling pockets 152 each includes a first surface 156, a second surface 158 and a third surface 160. The first surface 156, the second surface 158 and the third surface 160 are coupled together via curved or arcuate sections 162, such that each of the pair of pedestal coupling pockets 152 has rounded corners. The first surface 156 is substantially flat or planar, and extends along an axis that intersects an axis of which the second surface 158 extends. The second surface 158 is also substantially flat or planar. The third surface 160 is substantially flat or planar, and extends along an axis that is substantially perpendicular to the axis along which the second surface 158 extends. As will be discussed, each of the first surface 156, the second surface 158 and the third surface 160 cooperate with a portion of the pedestal 126 to couple the physiological characteristic sensor 122 to the pedestal 126.

The pair of introducer coupling slots 154 is in communication with the pair of pedestal coupling pockets 152. Generally, the pair of introducer coupling slots 154 each has a length defined along the body 144 that receives an entirety of an end of the respective one of the mating projections 138 to couple the sensor introducer 120 to the sensor base 142. In one example, each of the pair of introducer coupling slots 154 include a recess 163, which cooperates with a notched surface 138a (FIG. 4) of a respective one of the mating projections 138 to assist in coupling the sensor introducer 120 to the sensor base 142.

The adhesive patch 124 is coupled to the sensor base 142 and affixes the sensor base 142, and thus, the glucose sensor 140, to the skin of the user. The adhesive patch 124 is retained on, but not secured to, the pedestal 126 during packaging and shipping. The adhesive patch 124 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

With reference to FIG. 4, the adhesive patch 124 is substantially oval in shape, and has a first patch side 164 opposite a second patch side 166. The first patch side 164 includes an adhesive layer 164a having a first portion 168 and a second portion 170. The first portion 168 couples the second base side 148 of the sensor base 142 to the adhesive patch 124 to couple the sensor base 142 to the adhesive patch 124. The second portion 170 couples to the sensor electronics module (such as the wireless transmitter not shown), and may be covered with a backing liner 172.

The second patch side 166 includes a second adhesive layer 166a that couples the adhesive patch 124 and the physiological characteristic sensor 122 to the skin of the user. The second adhesive layer 166a may be coupled with a second backing liner 174, which is removable by the user prior to the deployment of the glucose sensor 140 at the sensor site. In certain instances, an additional adhesive layer or adhesive strip may also be provided on the bottom of the second backing liner 174 to temporarily secure the second backing liner 174 to the pedestal 126 during packaging, shipping, and handling. In this regard, additional adhesive layer or adhesive strip may be a double-sided adhesive element that maintains the second backing liner 174 in position atop the pedestal 126.

The adhesive patch 124 also defines a pair of pedestal coupling bores 176 and a sensor bore 178 that extend through the adhesive patch 124 from the first patch side 164 to the second patch side 166. The pair of pedestal coupling bores 176 each receives a respective portion of the pedestal 126 to retain or couple the adhesive patch 124 to the pedestal 126. The sensor bore 178 enables the glucose sensor 140 to pass through the adhesive patch 124 for subcutaneous placement into the body of the user.

The pedestal 126 receives and protects the insertion needle 136 of the sensor introducer 120 during packaging, shipping, and handling before deployment of the glucose sensor 140. The pedestal 126 also serves to assist a user in the removal of the sensor introducer 120 after the deployment of the glucose sensor 140. In one example, the pedestal 126 includes a first pedestal side 200 opposite a second pedestal side 202 and a pedestal sidewall 204 that interconnects the first pedestal side 200 with the second pedestal side 202. The pedestal 126 also includes a first pedestal end 206 opposite a second pedestal end 208. In certain embodiments, the pedestal 126 is composed at least in part from a plastic material. For the embodiment described here, the pedestal 126 is formed as a molded plastic component. In one example, the pedestal 126 is formed from ABS, nylon, an ABS/PC blend, PVC, polytetrafluoroethylene (PTFE), polypropylene, polyether ether ketone (PEEK), polycarbonate, or the like. In this example, the pedestal 126 is composed of polypropylene, and may be recyclable.

The first pedestal side 200 includes a surface 200a that receives the adhesive patch 124. Generally, the first pedestal side 200 is substantially oval in shape to correspond with the shape of the adhesive patch 124. The first pedestal side 200 includes a pair of posts 210 near the first pedestal end 206 and an inserter bore 212 spaced apart from the pair of posts 210 near the first pedestal end 206. Each of the pair of posts 210 extend for a height H, which is predetermined to enable each of the posts 210 to be received through the respective one of the pedestal coupling bores 176 and into the respective one of the pedestal coupling pockets 152 to couple the sensor base 142 to the pedestal 126.

Figure 5B:
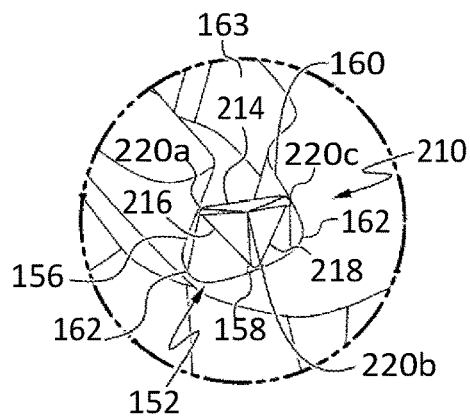
FIG. 5B is a detail view of the physiological characteristic sensor and the adhesive patch coupled to the pedestal of the physiological characteristic sensor assembly taken at 5B on FIG. 5A.
Figure 5C:
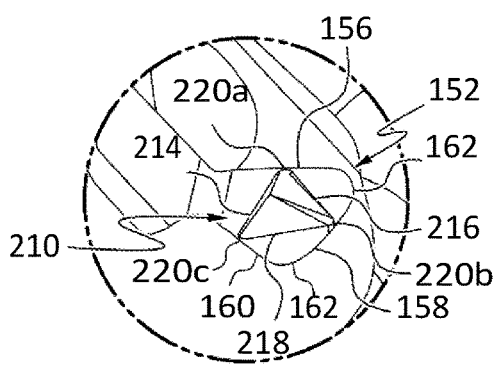
FIG. 5C is a detail view of the physiological characteristic sensor and the adhesive patch coupled to the pedestal of the physiological characteristic sensor assembly taken at 5C on FIG. 5A.
Figure 6:
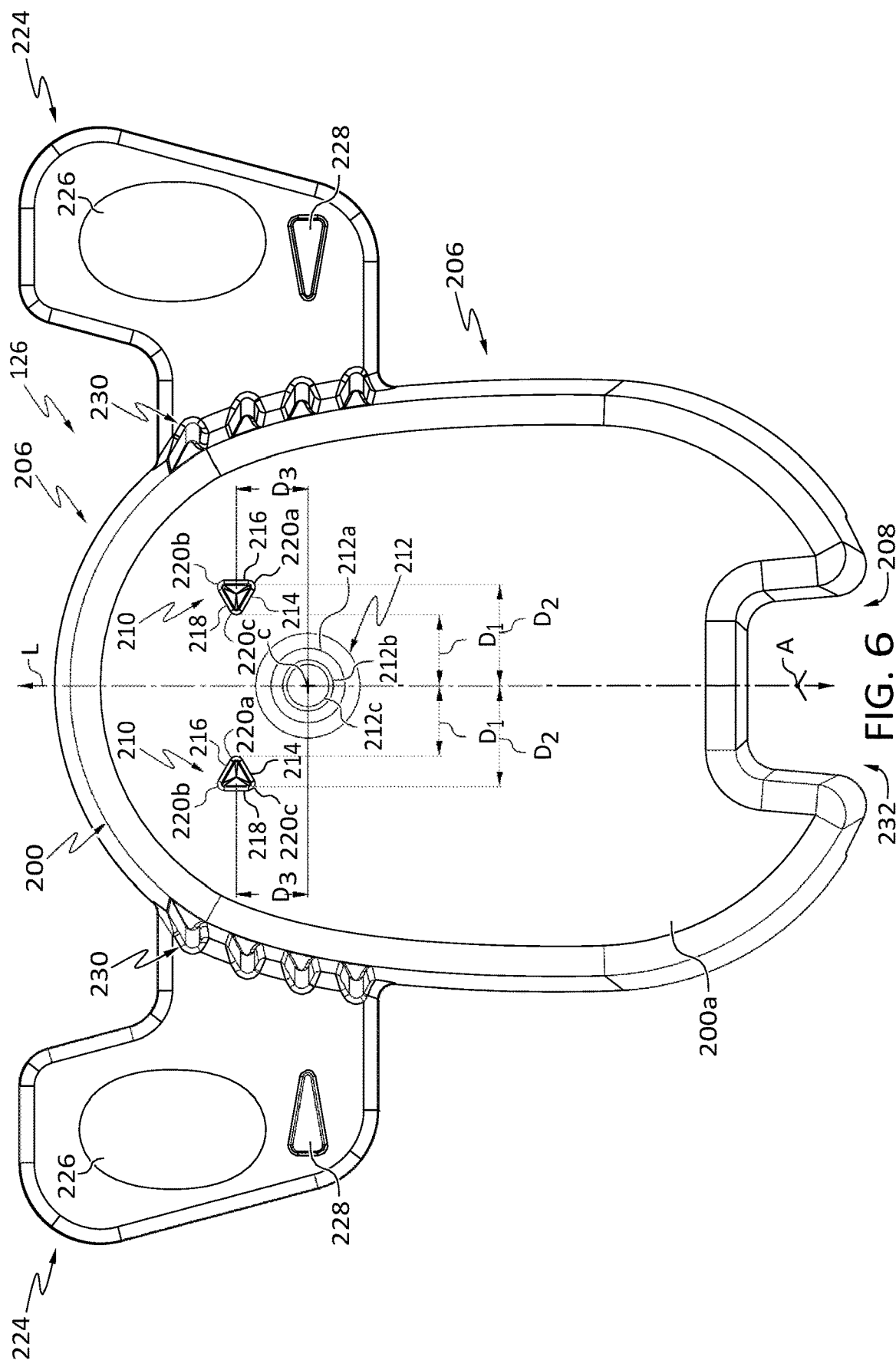
FIG. 6 is a top view of the pedestal of the physiological characteristic sensor assembly of FIG. 1.

With reference to FIG. 6, the first pedestal side 200 is shown in greater detail. As shown in FIG. 6, each of the posts 210 is substantially triangular. Each of the posts 210 has a first post side 214, a second post side 216 and a third post side 218. Each of the first post side 214, the second post side 216 and the third post side 218 cooperate to define three points of contact 220a, 220b, 220c that assist in securely coupling the sensor base 142 to the pedestal 126. With reference to FIGS. 5B and 5C, the first point of contact 220a contacts the first surface 156, the second point of contact 220b contacts the second surface 158 and the third point of contact 220c contacts the third surface 160. These three points of contact 220a, 220b, 220c form an interference fit with the pedestal coupling pockets 152 to securely retain the sensor base 142 on the pedestal 126 such that the insertion device 130 is required to remove the sensor base 142 from the pedestal 126.

In one example, the posts 210 are spaced a distance D1 from a center C of the inserter bore 212. In this example, the posts 210 may be rotated slightly relative to one another, such that the point of contact 220a of a first post 210a is spaced the distance D1 from the center C of the inserter bore 122 and the third point of contact 220c of a second post 210b is spaced the distance D1 from the center C of the inserter bore 122. The third point of contact 220c of the first post 210a is spaced a distance D2 from the center C of the inserter bore 122, and the first point of contact 220a of the second post 210b is spaced the distance D2 from the center C of the inserter bore 122. The posts 210 are each spaced apart from the center C of the inserter bore 122 by a distance D3. In one example, the distance D1 may range from about 0.17 inches (in.) to about 0.21 inches (in.), the distance D2 may range from about 0.23 inches (in.) to about 0.27 inches (in.), and the distance D3 may range from about 0.15 inches (in.) to about 0.19 inches (in.). Generally, the distances D1, D2 and D3 may vary based on the size of the sensor base 142 (FIG. 5A).

With reference back to FIG. 6, the inserter bore 212 is defined through the pedestal 126 from the first pedestal side 200 to the second pedestal side 202. The inserter bore 212 generally transitions in diameter from the first pedestal side 200 to the second pedestal side 202. In one example, the inserter bore 212 is a stepped bore, with a plurality of steps 212a, 212b, 212c that taper from a first diameter before the step 212a to a second diameter at the step 212c. In this example, the second diameter is less than the first diameter. Generally, the second diameter of the inserter bore 212 is smaller than the first diameter to provide a guide for the insertion needle 136 during deployment of the glucose sensor 140.

The second pedestal side 202 includes a pair of tabs or feet 224 near the first pedestal end 206. The feet 224 extend outwardly away from the pedestal sidewall 204, and include a graspable recess 226 and a graphical indicator 228. The graspable recesses 226 enable a user to position a finger on the respective one of the feet 224 to remove the sensor introducer 120 from the pedestal 126. The graphical indicator 228 provides a visual cue to the user for the removal of the pedestal 126 from the package tray 102 (FIG. 2). In one example, the graphical indicators 228 are recessed into the feet 224; however, the graphical indicators 228 may be raised on the feet 224, if desired.

The pedestal sidewall 204 extends about the perimeter of the pedestal 126. In one example, the pedestal sidewall 204 includes opposed grip surfaces 230 at the first pedestal end 206 and an introducer removal recess 232 at the second pedestal end 208. In one example, the grip surfaces 230 are spaced apart at the first pedestal end 206 so as to be positioned on the pedestal sidewall 204 adjacent to the feet 224. The grip surfaces 230 generally include a plurality of ribs 230a, which enable the user to grasp the pedestal 126 and remove the pedestal 126 from the package tray 102 (FIG. 2).

The introducer removal recess 232 is defined through the pedestal sidewall 204 so as to extend from the first pedestal side 200 to the second pedestal side 202. The introducer removal recess 232 extends along an axis A, which is substantially perpendicular to a longitudinal axis L of the pedestal 126. Generally, the introducer removal recess 232 is substantially symmetric about the axis A.

Figure 7:
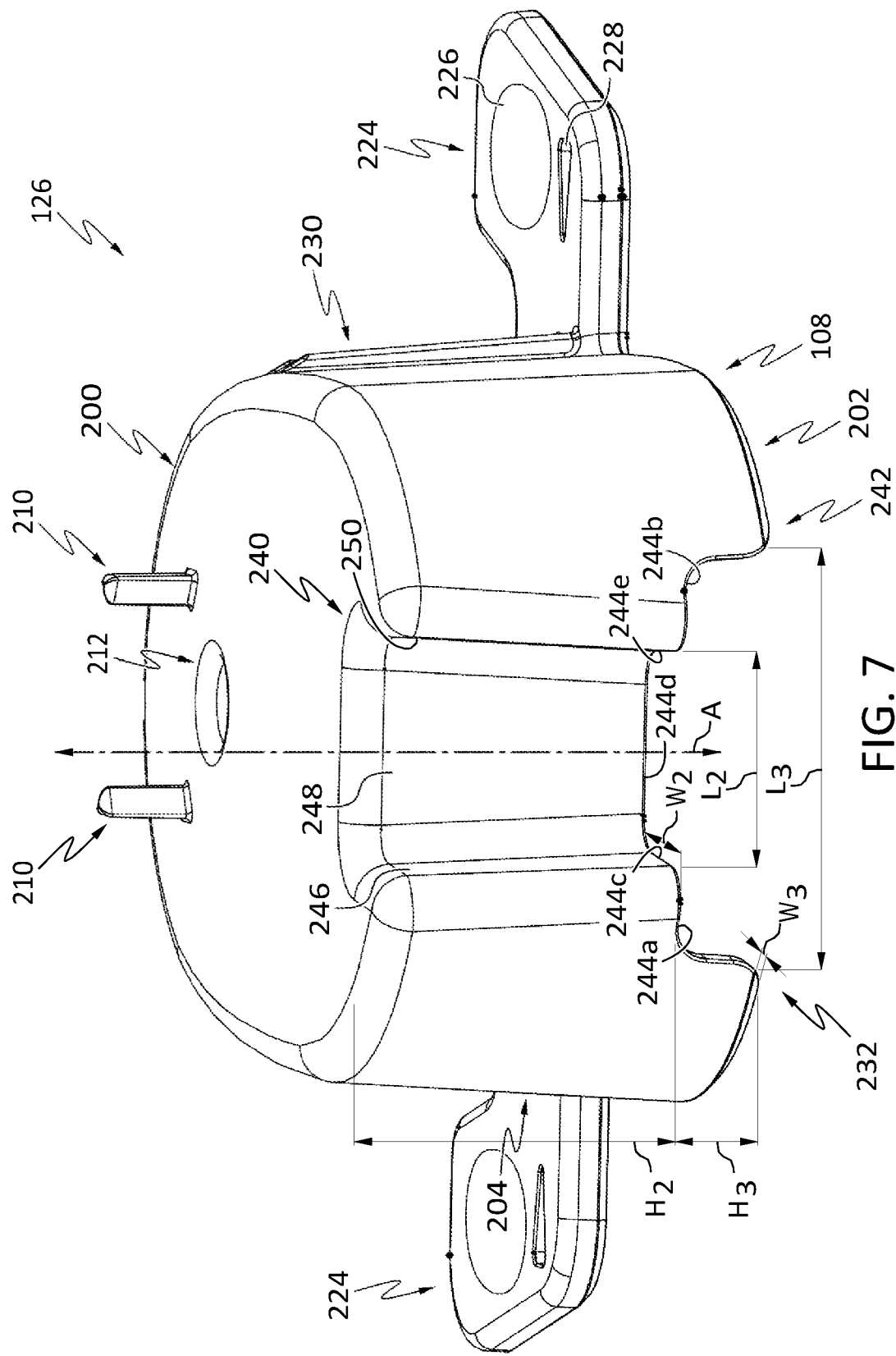
FIG. 7 is an end view of the pedestal of the physiological characteristic sensor assembly of FIG. 1.

With reference to FIG. 7, the introducer removal recess 232 is shown in greater detail. In one example, the introducer removal recess 232 has a first portion or introducer portion 240 and a second portion or base portion 242. Generally, the introducer portion 240 of the introducer removal recess 232 is positionable about the sensor introducer 120 and the base portion 242 of the introducer removal recess 232 is positionable over the first base side 146 of the sensor base 142. The introducer portion 240 extends from the first pedestal side 200 toward the second pedestal side 202 for a height H2. The introducer portion 240 is recessed into the pedestal sidewall 204 by a width W2. The width W2 is generally at least the same as or greater than a width W1 of the sensor introducer 120 (FIG. 4). The introducer portion 240 extends for a length L2 along a perimeter of the pedestal sidewall 204. Generally, the length L2 is greater than a length L4 of the sensor introducer 120 (FIG. 4).

The introducer portion 240 is substantially U-shaped, and includes a first wall 246, a second wall 248 and a third wall 250. Each of the first wall 246, the second wall 248 and the third wall 250 are interconnected to define the U-shape, which enables the sensor introducer 120 to be received within the introducer portion 240. Generally, the sensor introducer 120 is positionable within the introducer portion 240 of the introducer removal recess 232 to facilitate the removal of the sensor introducer 120 from the sensor base 142, as will be discussed. Stated another way, the introducer portion 240 provides a recess that receives the sensor introducer 120 to enable the base portion 242 to be positioned over the sensor base 142 to apply a holding force to the sensor base 142. The first wall 246 and the third wall 250 are coupled to the pedestal sidewall 204 via a rounded or arcuate surface.

Figure 8:
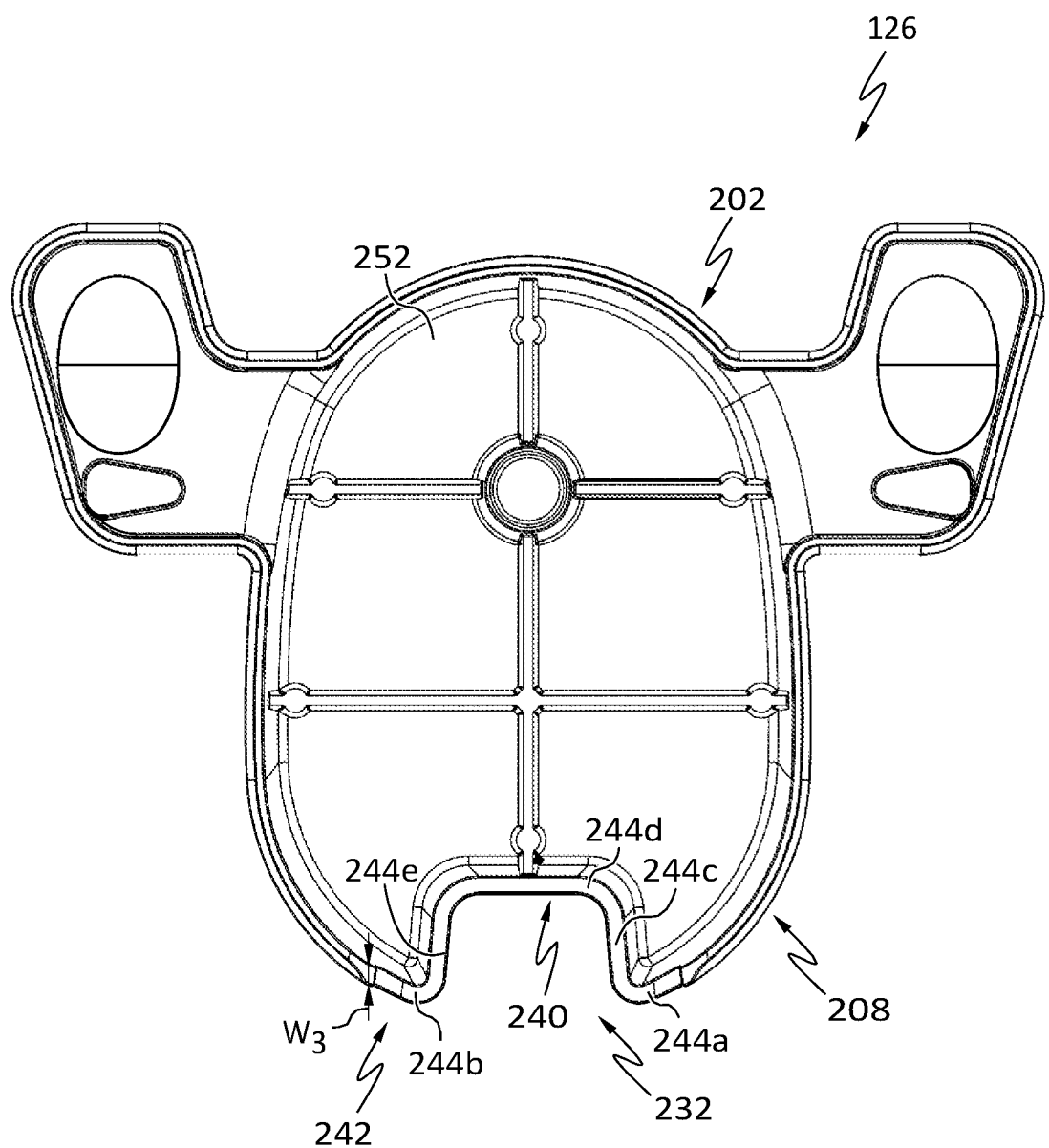
FIG. 8 is a bottom view of the pedestal of the physiological characteristic sensor assembly of FIG. 1.

The base portion 242 is in communication with the introducer portion 240. The base portion 242 is defined at the second pedestal side 202 and extends for a height H3 from the second pedestal side 202 toward the first pedestal side 200. The height H3 is less than the height H2 of the introducer portion 240 defined between the first pedestal side 200 and the second pedestal side 202. The base portion 242 has a length L3 along the perimeter of the pedestal sidewall 204, which is greater than the length L2 of the introducer portion 240. Generally, the length L3 is greater than a length L5 of the sensor base 142 (FIG. 5A). The base portion 242 has a width W3, which is less than the width W2 of the introducer portion 240. Generally, with reference to FIG. 8, the width W3 is the width of the pedestal sidewall 204. The difference in heights H2, H3 between the introducer portion 240 and the base portion 242 along a perimeter of the pedestal sidewall 204 defines a respective contact surface 244a, 244b, 244c, 244d, 244e along a perimeter of the introducer removal recess 232. The contact surfaces 244a-244e may apply a holding force to a portion of the sensor base 142 during the removal of the sensor introducer 120 from the sensor base 142 once the glucose sensor 140 has been deployed. As shown in FIG. 8, the pedestal 126 has a substantially hollow interior, such that a portion of the sensor base 142 may pass through the base portion 242 into an interior 252 of the pedestal 126 to assist the contact surfaces 244a-244e in applying a holding force to the sensor base 142 at a variety of positions of the sensor base 142, as will be discussed herein. Stated another way, the base portion 242 cooperates with the interior 252 of the pedestal 126 to enable the pedestal 126 to be positioned over the sensor base 142 at a variety of angles to enable the contact surfaces 244a-244e to apply a holding force to assist in removing the sensor introducer 120 from the sensor base 142.

With reference to FIG. 4, with the sensor introducer 120, the glucose sensor 140, the sensor base 142, the adhesive patch 124 and the pedestal 126 formed, the physiological characteristic sensor assembly 104 may be assembled. In one example, the glucose sensor 140 is coupled to the sensor base 142, and the physiological characteristic sensor 122 is coupled to the first portion 168 of the adhesive patch 124 such that the glucose sensor 140 passes through the sensor bore 178 and is at least partially received within the inserter bore 212 of the pedestal 126. The adhesive patch 124 is coupled to the pedestal 126 such that each of the pedestal coupling bores 176 are received over each of the respective posts 210, and the pedestal coupling pockets 152 are coupled to a respective one of the posts 210 to form the interference fit with the three points of contact 220a, 220b, 220c (FIG. 6). The sensor introducer 120 is coupled to the sensor base 142 by inserting the mating projections 138 into the introducer coupling slots 154.

Once assembled, with reference to FIG. 2, the physiological characteristic sensor assembly 104 is positioned within the interior cavity 108 of the package tray 102 such that the sensor introducer 120 is received within the retaining feature 110 and the grip surfaces 230 are adjacent to the opening 112. With the physiological characteristic sensor assembly 104 positioned within the package tray 102, the material 106 is applied over the opening 112 and cooperates with the sealing surface 114 to seal the physiological characteristic sensor assembly 104 within the package tray 102. The physiological characteristic sensor assembly 104 may then be shipped to a consumer or the user. Further detail regarding the manufacture and assembly of the packaging for the physiological characteristic sensor assembly 104 is described in U.S. Pat. No. 9,101,305 to Larson et al., which is incorporated herein by reference.

Once received by the consumer or user, in order to remove the physiological characteristic sensor assembly 104 from the package tray 102, the material 106 may be peeled away and removed to expose the interior cavity 108. The physiological characteristic sensor assembly 104 may be removed from the interior cavity 108 by gripping the grip surfaces 230 of the pedestal 126. With the physiological characteristic sensor assembly 104 removed from the package tray 102, the insertion device 130 may be used to insert the glucose sensor 140 into the body of the user.

Figure 9:
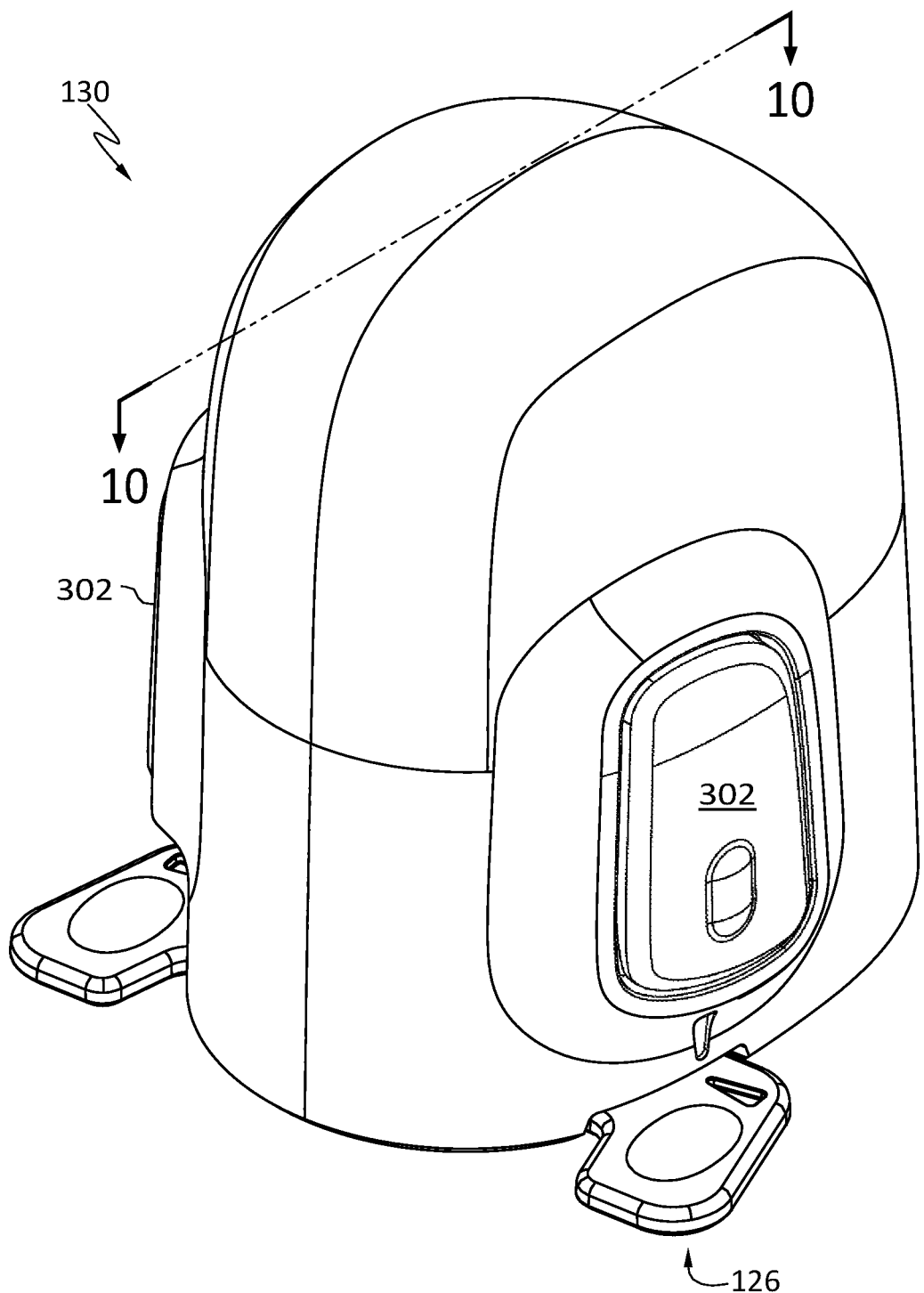
FIG. 9 is a perspective view of the insertion device positioned over the physiological characteristic sensor assembly of FIG. 1.
Figure 10:
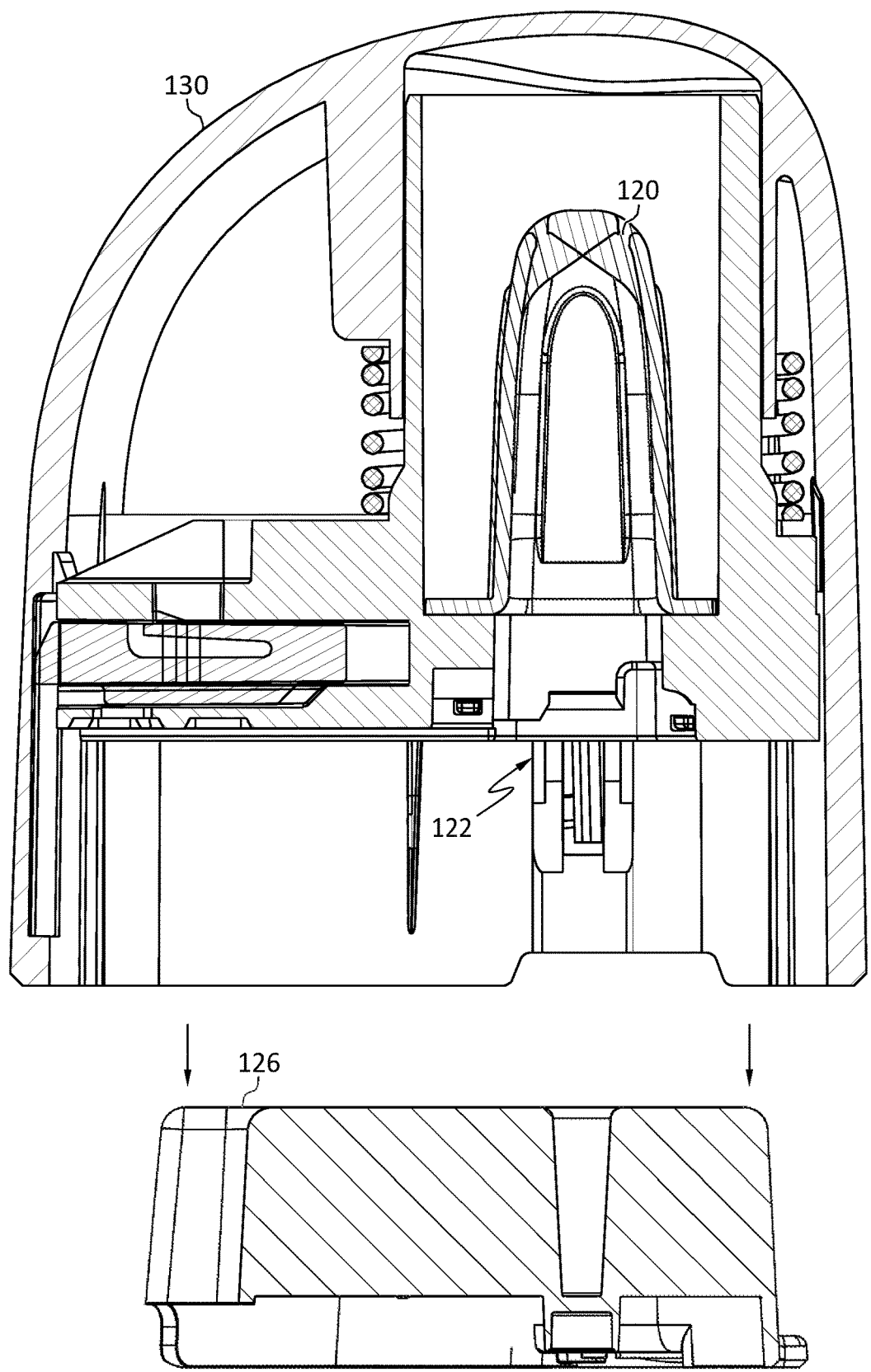
FIG. 10 is a schematic cross-sectional exploded view of the insertion device and the physiological characteristic sensor assembly taken from the perspective of line 10-10 in FIG. 9, which shows a sensor introducer, the physiological characteristic sensor and the adhesive patch removed from the pedestal.
Figure 11:
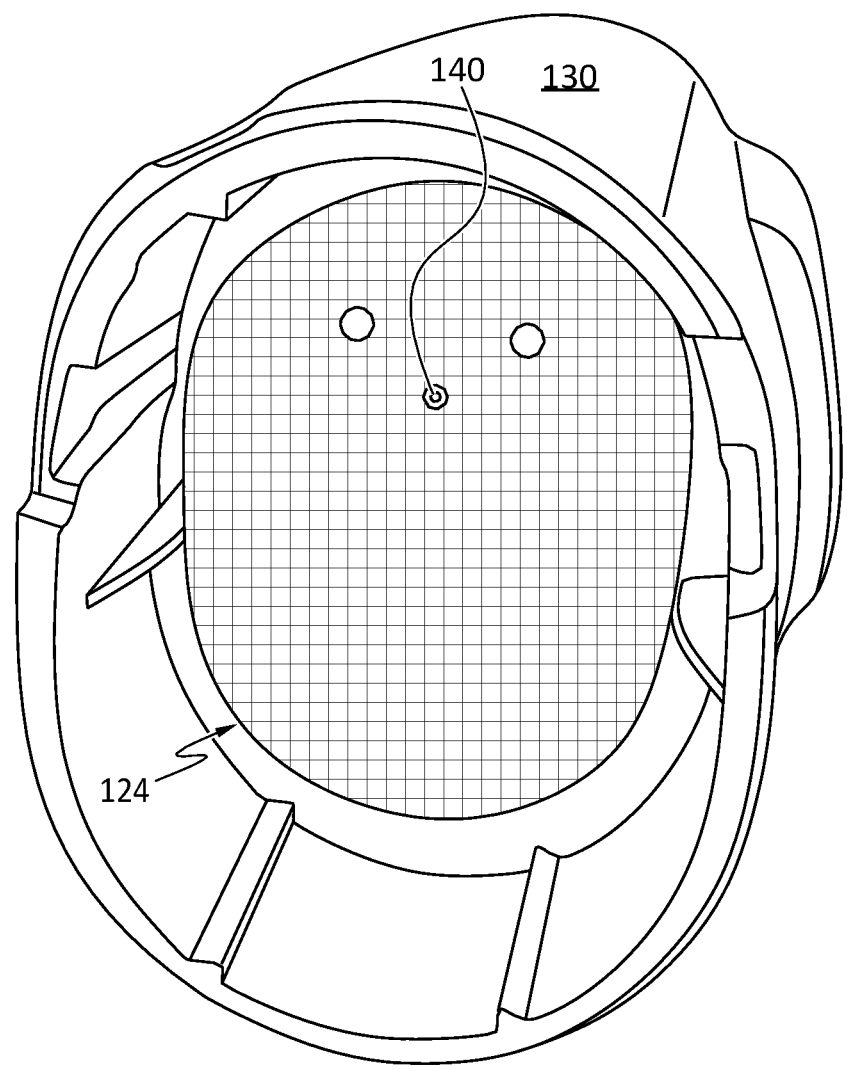
FIG. 11 is a rear view of the insertion device, which shows the adhesive patch removed from the pedestal of FIG. 1 for deployment of the physiological characteristic sensor.

An exemplary deployment methodology for the glucose sensor 140 will now be described with reference to FIGS. 9-11. FIG. 9 is a perspective view of an insertion device 130 that can be used with the physiological characteristic sensor assembly 104 (see FIG. 4). FIG. 10 is a phantom side view of the insertion device 130 in a loaded state, and FIG. 11 is a bottom perspective view of the insertion device 130 in a loaded state. In one example, the insertion device 130 is placed over the physiological characteristic sensor assembly 104 and is pressed down to engage the sensor introducer 120 and to spring-load the insertion needle 136. Thereafter, the pedestal 126 is separated from the other components of the physiological characteristic sensor assembly 104 by lifting the insertion device 130 away from the pedestal 126 while holding down the feet 224 of the pedestal 126 (see FIG. 4). Removal of the pedestal 126 causes the adhesive patch 124 to be removed from the surface 200a of the pedestal 126.

As depicted in FIG. 10 and FIG. 11, the remainder of the physiological characteristic sensor assembly 104 is retained within the interior of the insertion device 130, ready for deployment on the skin of the user. After removing the pedestal 126 from the assembly, the user moves the loaded insertion device 130 to the desired deployment location, holds the insertion device 130 against the skin, and actuates triggering buttons 302 of the insertion device 130 (see FIG. 7). Triggering the insertion device 300 moves the adhesive patch 124 into contact with the user's skin, and activates the insertion needle 136 to insert the glucose sensor 140 into the skin. Thereafter, the insertion device 130 is removed and separated from the sensor introducer 120 and the glucose sensor 140, which remains affixed to the skin by way of the adhesive patch 124.

Thus, after deployment of the glucose sensor 140 into the subcutaneous tissue with the insertion device 130, the sensor introducer 120 remains coupled to the sensor base 142. Generally, in order to remove the sensor introducer 120 from the sensor base 142, a force is needed to hold the sensor base 142 while pulling upward on the sensor introducer 120 to prevent accidental displacement of the glucose sensor 140. In certain instances, due to the deployment location, for example, it may be difficult for the user to apply a force to hold down the sensor base 142 while also applying a force to remove the sensor introducer 120. In these instances, the pedestal 126 may be employed by the user to apply the holding force to the sensor base 142 as shown in FIGS. 12 and 13.

Figure 12:
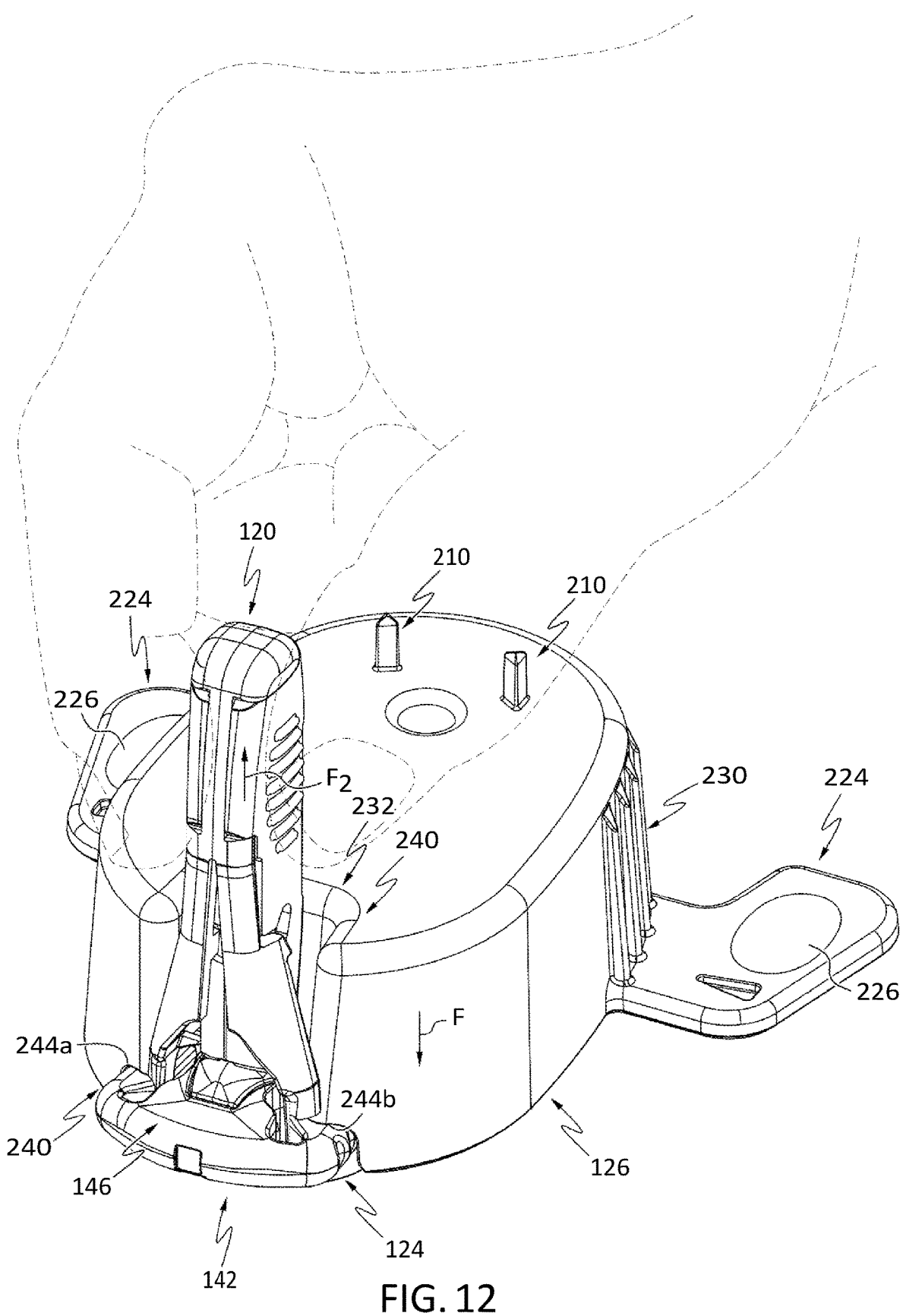
FIG. 12 is an end perspective view of the pedestal, which illustrates the pedestal positioned in one position of various positions for applying a holding force to a portion of the physiological characteristic sensor to enable removal of the sensor introducer.

In order to remove the sensor introducer 120, in one example, with reference to FIG. 12, the pedestal 126 is positioned over the sensor base 142 such that the first base side 146 of the sensor base 142 is adjacent to or in contact with one or more of the contact surfaces 244a-244e. The introducer portion 240 of the introducer removal recess 232 provides clearance for the pedestal 126 to be positioned over a portion of the first base side 146 without interfering with the removal of the sensor introducer 120. With the pedestal 126 positioned over a portion of the sensor base 142, the user may hold the pedestal 126 down with a portion of their hand, for example, thereby applying a holding force F to the sensor base 142 via one or more of the contact surfaces 244a-244e, and use their fingers to apply an upward force F2 to remove the sensor introducer 120 from the sensor base 142, without displacing the glucose sensor 140. Once the sensor introducer 120 is removed from the sensor base 142, the pedestal 126 may be removed from the sensor base 142 leaving the physiological characteristic sensor 122 coupled to the user via the adhesive patch 124. Thus, the introducer removal recess 232 of the pedestal 126 enables a user to remove the sensor introducer 120 from the sensor base 142 with a single hand, which enables the user to position the glucose sensor 140 in other hard to reach places, such as on an upper arm, without requiring assistance from another to remove the sensor introducer 120.

Figure 13:
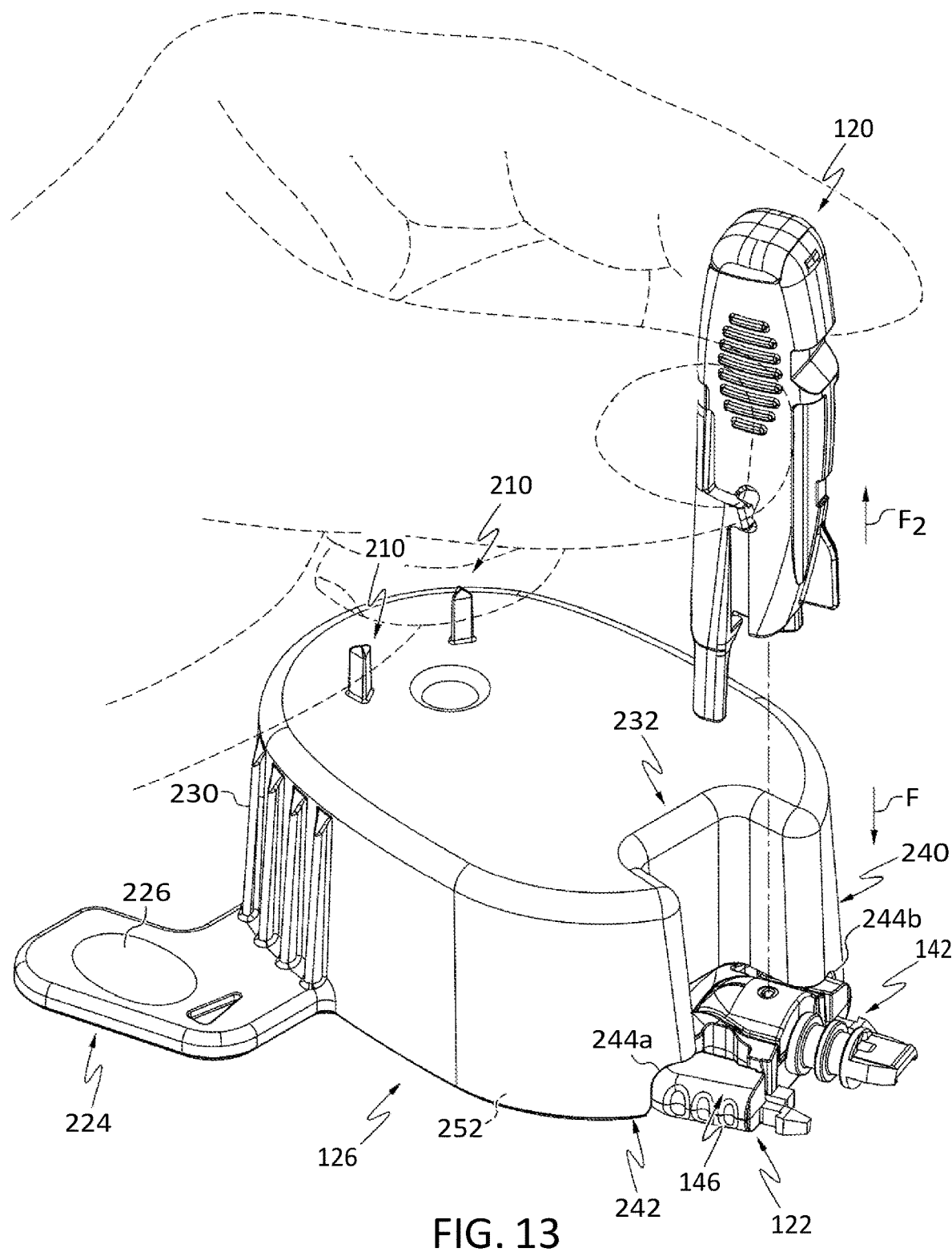
FIG. 13 is an end perspective view of the pedestal, which illustrates the pedestal positioned in another position of various positions for applying a holding force to a portion of the physiological characteristic sensor to enable removal of the sensor introducer.

Moreover, as illustrated in FIG. 13, the pedestal 126 need not be positioned over the first base side 146 of the sensor base 142 at a particular orientation. Rather, the base portion 242 of the introducer removal recess 232 cooperates with the interior 252 of the pedestal 126 to enable the pedestal 126 to be positioned over the sensor base 142 at a variety of orientations. As shown in FIG. 13, the user applies the holding force F to the pedestal 126, and one or more of the contact surfaces 244a-244e retain the sensor base 142 and the glucose sensor 140 at the sensor site. This enables the user, with a single hand, to apply the upward force F2 to remove the sensor introducer 120 from the sensor base 142 at various orientations of the pedestal 126.

With reference to FIG. 14, exemplary positions are shown in which the pedestal 126 may be positioned over the sensor base 142 to remove the sensor introducer 120 from the physiological characteristic sensor 122. As shown, the pedestal 126 may be positioned at various orientations to enable the contact surfaces 244a-244e to apply the holding force against the sensor base 142. Generally, any opposing two points of contact between the contact surfaces 244a-244e of the introducer removal recess 232 and the sensor base 142 that are approximately 0.5 inches (in.) apart on the sensor base 142 may be sufficient to hold down the sensor base 142 during a removal of the sensor introducer 120.

Thus, the pedestal 126 both protects the insertion needle 136 and the physiological characteristic sensor assembly 104 during shipping and handling, while also enabling a user to remove the sensor introducer 120 with a single hand after deployment of the glucose sensor 140. This enables the user to insert the glucose sensor 140 at unconventional or harder to reach places, such as an upper arm. Moreover, given the greater length L3 of the base portion 242 of the introducer removal recess 232 and the hollow interior 252 of the pedestal 126, the pedestal 126 is positionable over the first base side 146 of the sensor base 142 at numerous positions and orientations. The ability of the pedestal 126 to be positioned at numerous positions and orientations relative to the sensor base 142 provides the user with greater freedom to position the physiological characteristic sensor 122 at a desired sensor site, while still ensuring the user may remove the sensor introducer 120 with a single hand.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A physiological characteristic sensor assembly, comprising:
    a physiological characteristic sensor including a sensor coupled to a sensor base, the sensor base including a pair of pedestal coupling pockets each defining a plurality of planar surfaces and a pair of introducer coupling slots, each one of the pair of introducer coupling slots in communication with a respective one of the pair of pedestal coupling pockets;
    an adhesive patch coupled to the physiological characteristic sensor; and
    a pedestal removably coupled to the physiological characteristic sensor, the pedestal including a first side opposite a second side and a first end opposite a second end, with a sidewall that interconnects the first side and the second side and a longitudinal axis defined along the pedestal from the first end to the second end, the pedestal including:
        a pair of posts that extend outwardly from a surface of the first side proximate the first end, each of the pair of posts defining a plurality of points of contact to form an interference fit with the sensor base in a first position in which the physiological characteristic sensor is coupled to the pedestal, the pair of posts rotated relative to one another, with each of the plurality of points of contact of each of the pair of posts in contact with a respective one of the plurality of planar surfaces of the pair of pedestal coupling pockets of the sensor base in the first position; and
        a removal recess defined through the sidewall at the second end having a first portion in communication with a second portion, the removal recess extends from the first side to the second side along an axis that is perpendicular to the longitudinal axis of the pedestal, the first portion having a first length that is less than a length of the second portion along a perimeter of the sidewall, the first length and the length of the second portion defined perpendicular to the axis of which the removal recess extends, the removal recess defines at least one first contact surface along the first length at the second side and at least one second contact surface along the second length at the second side, and the second portion is configured to be positionable over the sensor base such that the at least one first contact surface and the at least one second contact surface apply a force to the sensor base in a second position in which the physiological characteristic sensor is uncoupled from the pedestal and deployed onto an anatomy.

2. The physiological characteristic sensor assembly of claim 1, wherein the pair of posts each extend outwardly from the surface of the first side so as to be parallel to the axis of which the removal recess extends.

3. The physiological characteristic sensor assembly of claim 1, wherein the removal recess is symmetric about the axis of which the removal recess extends.

4. The physiological characteristic sensor assembly of claim 1, further comprising a sensor introducer coupled to the pair of introducer coupling slots of the sensor base in the first position, the sensor introducer to introduce the sensor into the anatomy.

5. The physiological characteristic sensor assembly of claim 4, wherein sensor base has a first base side opposite a second base side, the second base side is coupled to the adhesive patch and the first portion of the removal recess is configured to be positionable about the sensor introducer and the second portion of the removal recess is configured to be positionable over the first base side of the sensor base in the second position.

6. The physiological characteristic sensor assembly of claim 1, wherein the first portion has a first height along the axis of which the removal recess extends and the second portion has a height defined between the first side and the second side of the pedestal along the axis of which the removal recess extends, and the height of the second portion is less than the first height.

7. The physiological characteristic sensor assembly of claim 1, wherein the first portion has a first width and the second portion has a width defined from a perimeter of the pedestal at the second end, the first width greater than the width of the second portion such that the first portion is indented into the pedestal, with the first width and the width of the second portion perpendicular to the axis of which the removal recess extends.

8. The physiological characteristic sensor assembly of claim 1, wherein the adhesive patch is couplable to the first side of the pedestal and the adhesive patch defines a pair of coupling bores to receive a respective one of the pair of posts.

9. The physiological characteristic sensor assembly of claim 1, wherein the physiological characteristic sensor is a glucose sensor.

10. A physiological characteristic sensor assembly, comprising:
a physiological characteristic sensor including a sensor coupled to a sensor base, the sensor base including at least one pedestal coupling pocket defining a plurality of planar surfaces and at least one introducer coupling slot in communication with the at least one pedestal coupling pocket;
an adhesive patch coupled to the physiological characteristic sensor; and
a pedestal removably coupled to the physiological characteristic sensor, the pedestal including a first side opposite a second side and a first end opposite a second end, with a sidewall that interconnects the first side and the second side and a longitudinal axis defined along the pedestal from the first end to the second end, a surface of the first side configured to receive the adhesive patch in a first position in which the physiological characteristic sensor is coupled to the pedestal, the pedestal including:
at least one post that extends outwardly from the surface of the first side near the first end, the at least one post defining a plurality of points of contact configured to form an interference fit with the sensor base in the first position, with each of the plurality of points of contact in contact with a respective one of the plurality of planar surfaces of the at least one pedestal coupling pocket of the sensor base in the first position; and
a removal recess defined through the sidewall at the second end having a first portion in communication with a second portion, the removal recess extends from the first side to the second side along an axis that is perpendicular to the longitudinal axis of the pedestal, the removal recess defines at least one first contact surface along the first length at the second side and at least one second contact surface along the second length at the second side, and the second portion is configured to be positionable over the sensor base such that the at least one first contact surface and the at least one second contact surface apply a force to the sensor base in a second position in which the physiological characteristic sensor is uncoupled from the pedestal and deployed onto an anatomy,
wherein the at least one post extends from the first side so as to be parallel to the axis of which the removal recess extends.

11. The physiological characteristic sensor assembly of claim 10, wherein the first portion has a first height along the axis of which the removal recess extends and the second portion has a height defined between the first side and the second side of the pedestal along the axis of which the removal recess extends, the height of the second portion is less than the first height, and the first portion has a first length that is less than a length of the second portion along a perimeter of the sidewall.

12. The physiological characteristic sensor assembly of claim 10, wherein the first portion has a first width and the second portion has a second width defined from a perimeter of the pedestal at the second end, the first width greater than the second width such that the first portion is indented into the pedestal, with the first width and the second width perpendicular to the axis of which the removal recess extends.

13. The physiological characteristic sensor assembly of claim 10, wherein the adhesive patch is couplable to the first side of the pedestal in the first position and the adhesive patch defines at least one coupling bore through which the at least one post is received.

14. The physiological characteristic sensor assembly of claim 10, further comprising a sensor introducer coupled to the at least one introducer coupling slot of the sensor base to introduce the sensor into the anatomy, the sensor base having a first base side opposite a second base side, the second base side is coupled to the adhesive patch, and the first portion of the removal recess is configured to be positionable about the sensor introducer and the second portion of the removal recess is configured to be positionable over the first base side of the sensor base in the second position.

15. The physiological characteristic sensor assembly of claim 1, wherein each of the pair of posts is triangular.

16. The physiological characteristic sensor assembly of claim 10, wherein the at least one post is triangular.

\* \* \* \* \*